United States Patent [19]

Franks et al.

[11] Patent Number: 4,917,804
[45] Date of Patent: Apr. 17, 1990

[54] METHOD AND VESSEL FOR SEPARATION OF CRYOGLOBIN

[75] Inventors: Stephen H. Franks, Hopkinton; David M. Dillon, Dover; Read S. McCarty, Hingham, all of Mass.

[73] Assignee: Baxter International Inc., Deerfield, Ill.

[21] Appl. No.: 925,318

[22] Filed: Oct. 31, 1986

[51] Int. Cl.$^4$ ............................................. B01D 21/26
[52] U.S. Cl. ................................. 210/737; 210/321.6; 210/472; 210/515; 210/539; 210/782; 210/789; 422/101; 422/102; 424/101; 494/37; 530/380; 530/383; 530/830; 604/410
[58] Field of Search .................. 604/4, 6, 406, 408, 604/410; 494/16, 17, 18, 37; 422/102, 101; 210/737, 782, 787, 360.1, 361, 369, 380.1, 789, 514, 515, 539, 472, 321.6, 774; 424/101; 530/380, 383, 830

[56] References Cited

U.S. PATENT DOCUMENTS

| | | |
|---|---|---|
| 3,481,712 | 12/1969 | Bernstein ............................ 422/102 |
| 3,545,671 | 12/1970 | Ross . |
| 3,750,645 | 8/1973 | Bennett et al. . |
| 3,870,042 | 3/1975 | Viguier . |
| 3,897,902 | 8/1975 | Yanez, Jr. ....................... 210/789 X |
| 3,986,506 | 10/1976 | Garber et al. ....................... 604/406 |
| 4,040,959 | 8/1977 | Berman et al. . |
| 4,141,887 | 2/1979 | Seufert . |
| 4,310,488 | 1/1982 | Rahm et al. ....................... 422/102 |
| 4,335,730 | 6/1982 | Griffin ............................ 422/102 X |
| 4,364,903 | 12/1982 | Bittings ............................. 422/101 |
| 4,483,825 | 11/1984 | Fatches ........................... 422/101 X |
| 4,537,308 | 8/1985 | Hollander, Jr. . |
| 4,588,554 | 5/1986 | Kaartinen et al. . |
| 4,617,009 | 10/1986 | Ohlin et al. ............................ 494/21 |
| 4,698,311 | 10/1987 | Hall et al. ............................ 210/789 |
| 4,720,284 | 1/1988 | McCarty ............................... 494/37 |

OTHER PUBLICATIONS

"Now the Way is Clear ... with the Cutter Leukotrap Platelet Pooling System", Miles Laboratories (1985), CB-676.

Primary Examiner—W. Gary Jones
Attorney, Agent, or Firm—Paul C. Flattery; Bradford R. L. Price; Robert M. Barrett

[57] ABSTRACT

A set for the isolation of cryoprecipitate includes a hollow vessel with a closed first end, a second end and a longitudinal axis, and a nipple extending from and closing the second end, said nipple enclosing a volume of approximately 2 to 5 percent of the volume of the hollow vessel. In one embodiment, the vessel is formed of a semi-rigid material and the first end is closed by a cap containing a micro-porous filter for venting the vessel. In another or further embodiment, the nipple has a tapered tip portion which may be sliced off to permit extrusion of the isolated cryoprecipitate by squeezing the vessel. In a different further embodiment, the nipple has a twist-lockable connector, for attachment to a syringe or to an applicator tip. In yet another embodiment a piston mounts on the cap within the vessel for directly extruding separated cryoprecipitate from the nipple. Preferably the set includes plural vessels, each connected to a common sterile docking connector and having a total volume of approximately 250 ml, for processing the plasma from one unit of whole blood. Methods for the isolation of cryoprecipitate using a set according to the invention, and for the surgical application of the isolated precipitate are shown.

9 Claims, 4 Drawing Sheets

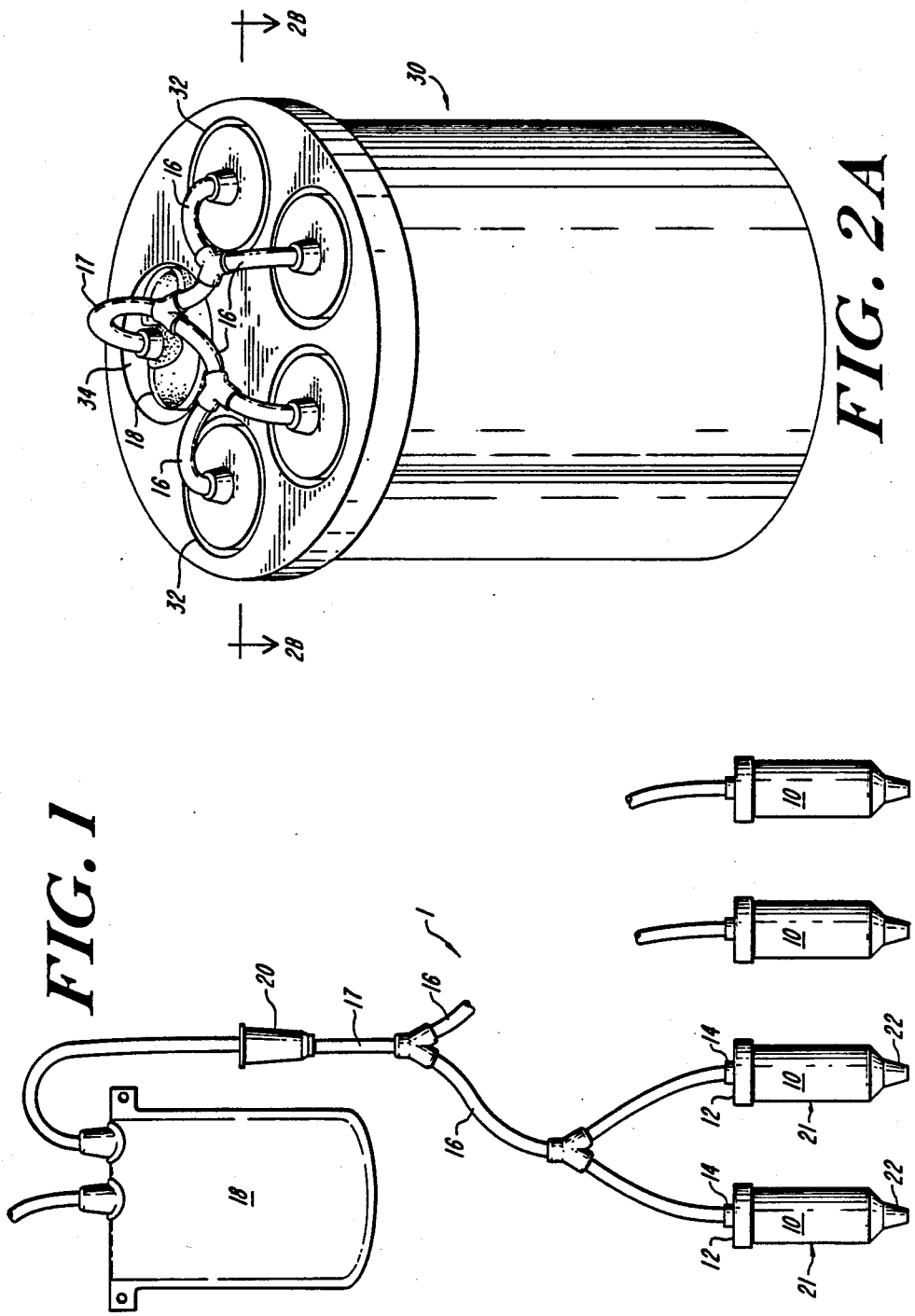

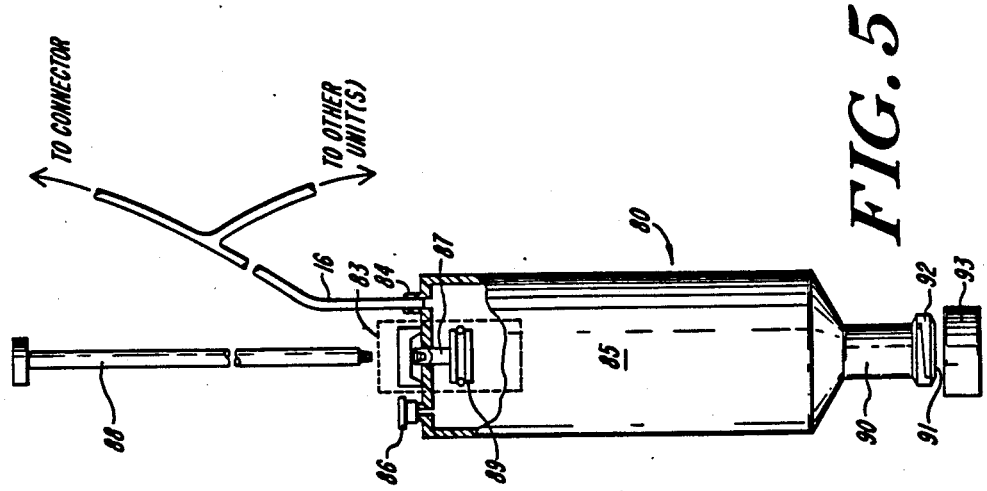

METHOD AND VESSEL FOR SEPARATION OF CRYOGLOBIN

BACKGROUND OF INVENTION

This invention relates to blood separation methods and apparatus, and more particularly to the isolation of cryoprecipitate or cryoglobin.

Cryoprecipitate, isolated from blood plasma, is rich in clotting factors. For this reason, it has long been used for the treatment of hemophilia. More recently, it has been proposed to make a "fibrin glue" for sealing surgical joins using a multi-part mixture of cryoprecipitate, thrombin and calcium chloride. Cryoprecipitate alone has also been reported as suitable for such use, especially as a natural clotting sealant around sutured joins of arterial or veinous tissue. Although of lesser tensile strength than a fibrin glue composition, approximately 2 to 3 percent of plasma may be isolated as cryoprecipitate, and the isolation may be performed in a hospital blood bank. Thus, autologous aliquots of "cryo" for surgical use may be prepared. This offers great promise in heart surgery, where suture bleeding, and patient cross reactions to blood-derived agents are both particularly grave problems.

The standard procedure for isolating cryoprecipitate uses a conventional phlebotomy set. The blood is drawn and anticoagulated, and centrifuged to separate the plasma. The plasma is expressed to the plasma bag, which is then sealed. The plasma bag is then frozen and thawed, which results in the precipitation of cryoprecipitate as a whitish factor. The cryoprecipitate is then separated from the plasma by centrifuging the plasma bag, and expressing the lighter cryo-poor fraction from the bag, leaving the cryoprecipitate fraction of 4–8 milliliters in the bag. Alternatively, the thawed plasma may be centrifuged in one or more centrifuge tubes, isolating the cryoprecipitate as a highly viscous plug in the bottom of each tube.

The separated material may be used by daubing about a surgical site with a spatula, or may be refrozen and thawed to result in a thinner, injectable form of cryoprecipitate such as used for the aforementioned treatment of hemophilia.

OBJECTS AND SUMMARY OF THE INVENTION

It is an object of the invention to provide an improved method and vessel for the isolation of cryoprecipitate.

It is another object of the invention to provide a vessel for the isolation of cryoprecipitate which is adapted for aseptic or sterile docking and storage.

It is another object of the invention to provide a vessel for the isolation of cryoprecipitate which is also an applicator for the topical application of the cryoprecipitate to a surgical site.

These and other desirable features are obtained in a set for the isolation of cryoprecipitate having a hollow cylindrical vessel with a first closed end, a second end and a longitudinal axis, the first end having a port with a sterile docking connector for transferring plasma between the vessel and a plasma bag, and the second end having a nipple extending from and closing the second end. Preferably the nipple has a generally cylindrical shape and encloses a volume of approximately 2 to 5 percent of the volume of the vessel.

In one embodiment, the vessel is formed of a semi-rigid material and the first end is closed by a cap containing a micro-porous filter for venting the vessel during transfer of plasma through the port. In another or further embodiment, the nipple has a tip portion which may be sliced off to permit extrusion of the isolated cryoprecipitate by squeezing the vessel. In a different further embodiment, the nipple has a twist-lockable connector, such as a Luer fitting, for attachment to a syringe or to an applicator tip. A presently preferred embodiment includes plural vessels, each with an end cap and a nipple, wherein all the end caps are connected to a common sterile docking connector. The total volume of the plural vessels is approximately 250 ml, for holding the plasma from one unit of whole blood.

A method for the isolation of cryoprecipitate according to the invention includes the steps of separating plasma from whole blood transferring the plasma to the one or more vessels according to the invention, freezing and thawing the plasma, and centrifuging the vessels to isolate the cryoprecipitate in the nipple end of each vessel. After isolation according to the invention, the cryo-poor plasma is decanted from each vessel through its port, and the vessels, each with a plug of cryoprecipitate in its nipple end, are stored as sterile aliquots for surgical or medical use. In a further method according to the invention, the cryoprecipitate is applied directly to a surgical site by extruding it from the nipple.

BRIEF DESCRIPTION OF THE DRAWINGS

FIG. 1 is a schematic illustration of the invention with a plasma bag of a phlebotomy set;

FIGS. 2A, 2B show a plan view from above, and a vertical section, respectively, of the set of FIG. 1 in a support fixture for centrifuging;

FIG. 5 shows another embodiment of the invention with an integral extrusion mechanism.

DETAILED DESCRIPTION OF ILLUSTRATED EMBODIMENTS

Figure 4:
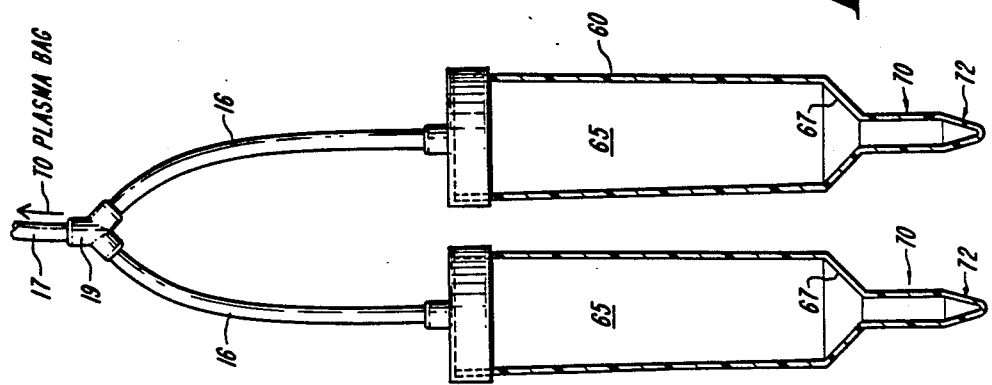
FIG. 4 shows a section of another embodiment of the invention.

FIG. 1 shows a schematic illustration of a set 1 according to a basic embodiment of the invention. Set 1 includes a plurality of vessels 10 each having an inlet end 12 with a port 14. A branch tube 16 runs from each port 14 to a common tube 17 which connects to a plasma bag 18. The plasma bag 18 may be the plasma receiving bag of a conventional phlebotomy set, and tube 17 may connect in a conventional manner to such bag so as to form a sterile system. Alternatively, the entire set including bag 18 tubes 17, 16 and vessels 10 may be formed as a sterile sealed unit. Preferably, tube 17 connects to plasma bag 18 via a spike or other fitting 20, which is preferably a sterile docking fitting.

Each vessel 10 has a generally cylindrical body 20 which extends from an inlet cap 12 which closes one end to a collection end 22 with the shape of a small substantially cylindrical nipple which closes the other end of the cylinder. The nipple structure is located to receive the densest faction of plasma during centrifuging, and is dimensioned to accommodate the amount of cryoprecipitate yielded by the volume of plasma held by the vessel 10.

Figure 2B:
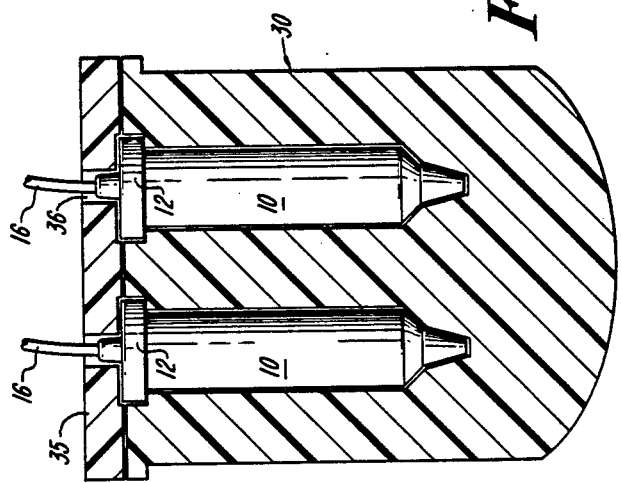

FIGS. 2A, 2B show a top perspective view and a section, respectively of a four vessel set according to FIG. 1 held in a support fixture for centrifuging. Vessels 10 are each inserted in a cylindrical well 32 of the fixture 30, and tubes 16, 17 connect the vessels to the plasma bag 18. As discussed in connection with the method for practicing the invention, below, the contents of bag 18 have been expressed into the vessels 10 and bag 18, which is empty, is rolled up and inserted in another recess 34 of fixture 30. FIG. 2B is a vertical section along the planes indicated in FIG. 2A, through the fixture 30 and passing through two of the recesses 32. As shown, the cylindrical wells 32 of the fixture 30 have solid walls defining a contour identical to that of the vessels 10 so that each vessel is rigidly supported about its entire outside surface. A cover plate 35 having slots for the passage of tubes 16, 17 therethrough may be fitted over the fixture in the centrifuge bucket so as to provide a complete pressure resisting housing around the set during centrifuging.

The method of separating cryoprecipitate according to the invention proceeds as follows. First, after blood is drawn, anticoagulated and separated, the plasma is expressed off into a plasma bag 18. The plasma is then expressed into the vessels 10 which are dimensioned to receive the entire volume of plasma from one unit of whole blood. According to standard blood bank practice in the United States, a unit of whole blood has a blood volume of about 450 milliliters, and yields 200–250 milliliters of plasma. Thus, for example, there may be four vessels 10 each having a volume of approximately 60 milliliters, three vessels each having a volume in the range of 80 milliliters or even a single large 250 milliliter vessel. Either before or after such transfer, the plasma is frozen and then thawed to precipitate out the cryoprecipitate. A good yield is obtained by completely freezing to minus thirty degrees C, thawing in a refrigerator at two to six degrees C and centrifuging at two to five thousand g (RCF) for ten to thirty minutes.

Vessels 10 and the empty plasma bag 18 are then placed in the fixture 30 described above and centrifuged at a speed and for a time sufficient to separate out the cryoprecipitate as a viscous mass in the nipple 22. The centrifuge is then stopped, the vessels 10 and bag 18 removed therefrom, and the cryo-poor plasma faction is decanted from each vessel back into the plasma bag 18, whence it may be returned to the donor or otherwise used. Each vessel 10 then contains one aliquot of cryoprecipitate from its corresponding volume of plasma.

These aliquots may then be stored, processed or used immediately.

It will be appreciated that with a unitary set as shown in FIG. 1, or a tubing and vessel set adapted for sterile docking, the units of cryoprecipitate thus isolated will be sterile and may be banked for surgical use. In particular, since the separation is accomplished using a normal blood bank centrifuge with the set 1 and fixture 30, cryoprecipitate may be prepared from a patient's own blood in preparation for a surgical procedure on the patient weeks in advance, substantially lessening the risks of infection or rejection reactions inherent in the use of pooled blood products or in the use of blood products from other donors.

Figure 3:
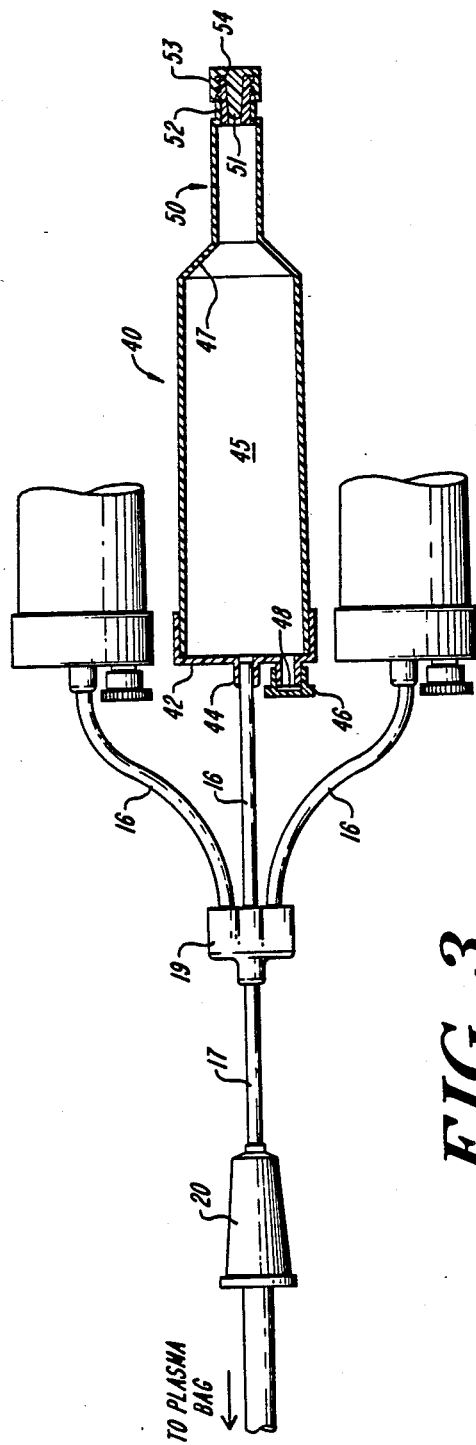
FIG. 3 shows a schematic section of a preferred embodiment of a three-vessel sterile docking set.

FIG. 3 shows a partial view and section of a preferred embodiment of a three vessel sterile docking set for the isolation of cryoprecipitate according to the invention. In this embodiment, a capped bag spike 20 connects to tube 17 which communicates via a trifurcated adaptor manifold 19 to three tubes 16, which extend to respective collection vessels 40. A suitable adaptor manifold 19 is a Medex part no. B-1450-09. Each vessel 40 has a generally cylindrical body 45 with a cap 42 at one end and a nipple portion 50 at the other end. Body 45 is preferably formed of a semi-rigid material such as a thick walled polyvinyl chloride plastic, and has an interior volume in the range of 60 to 80 milliliters. End cap 42 is formed with an inlet port 44 and also a vent 46 which permits the displacement of air when plasma is transferred from a plasma bag to the vessel or vice versa. Vent 46 includes a hydrophobic micro-porous filter 48 having a pore size in the range of 0.45 microns for preventing the influx of contaminants while permitting gas to vent therethrough. A suitable filter is a membrane-type filter sold by the Burron Medical Products company of Pennsylvania as their filter membrane, part no. A-700 4020. Cap 42 is cemented or otherwise bonded to body 45 for sealing the end thereof.

At the other end of the vessel body 45 a curved or funnel shaped wall 47 leads smoothly into the nipple end 50 which has a generally cylindrical or substantially tubular shape and is dimensioned so as to have an interior volume in the range 2 to 5 percent of the volume of the body 45. Nipple 50 extends to an outlet end which is adapted for connection to a separate device for transfer of the separated cryoprecipitate or for direct application of the separated precipitate to a surgical site. In this embodiment, nipple 50 has an interior wall 51 at its extreme tip which is tapered as a female Luer lock so that a syringe may be directly attached to the tip to draw out the separated precipitate and to allow a surgeon to use a syringe as an applicator of the precipitate to a surgical site. Nipple 50 has an external wall 52 which is threaded as a male twist-lock connection, i.e., a male Luer fitting. Nipple 50 is thus also adapted for directly connecting to a twist lockable cannula or needle for directly extruding the cryoprecipitate onto a surgical site. A Luer lock cap 53, such as the Luer cap part no. B-1500-30 sold by the Medex company of Ohio having a twist-lock inner surface 54 closes the end of the nipple so that the entire set comprising vessel(s) 40 with spike and supply tubes 16, 17 constitutes a sterile closed system.

FIG. 4 shows another embodiment of the invention having vessels 60, in a similar sectional view. Two vessels are shown connected to a common manifold 19 and supply tube 17. Although two vessels are shown, any number (n) may be used. In this embodiment, vessel 60 includes a cylindrical body 65 having a volume of approximately 250/n milliliters, and tapering at wall 67 to a nipple Portion 70. Nipple portion 70 has a conically pointed nose 72 which may be sliced off, in the manner of caulking cartridge, so as to provide an outlet for the separated cryoprecipitate therein. Vessel 60 is formed of a semi-rigid but sufficiently flexible material, such as a 0.030 to 0.040 inch thick flexible PVC, so that with the inlet tube 16 sealed closed, the vessel 60 may be squeezed by hand to extrude the precipitate from the end 72 of the vessel. The conical end has a taper of approximately fifteen degrees, terminating in a tip having an inner spherical radius in the range of (0.05) to (0.10) inches, thus providing both a high degree of operator visibility, and a fine extrusion filament of precipitate when so squeezed. No vent structure is shown, although a vent similar to the structure 46, 48 of FIG. 3, or a simple return breather tube extending from the vessel 60 to the plasma bag may be employed during the plasma filling and separating steps. Such tube or other vent is then sealed, clamped or capped prior to using the vessel 60 as a pressurized extruding device.

FIG. 5 shows yet another embodiment of a vessel 80 according to the invention having a body 85 and a nipple portion 90. As in the device of FIG. 3, nipple 90 has an open tip with an inner surface 91 and an outer surface 92 configured for twist lockable connection to a mating Luer fitting. A cap 93 closes the end. In his embodiment, the body of vessel 80 is formed of a substantially rigid material such as a polycarbonate plastic, and has an end cap 82 which includes, in addition to a vent 86 and an inlet port 84, a hermetically mounted piston structure 83. Piston structure 83 includes a soft rubber or similar piston 86 having a shank 87 which extends through the cap 82 and is hermetically sealed by a removable lock cap 84. Piston structure 83 is centered over the cylindrical nipple 90. A separate plunger 88 is provided, and after separation of the cryoprecipitate, the supply tube 16 may be severed and sealed so that the vessel 80, containing a sterile aliquot of cryoprecipitate, may be stored and used directly as a surgical applicator. For such use, the removable lock cap 84 is unscrewed, the plunger push rod 88 is screwed into the shank 87 of the piston, and the piston is pushed downward into the interior bore of nipple 90 to extrude the precipitate. Shank 87 may be fashioned as a break-away portion of the cap, or as a flexible stopper-like fitting which is driven through from a sealing position in a mating hole in the cap by plunger pressure.

Each of the above described embodiments either includes a closed sterile phlebotomy set, or is adapted for sterile docking with the plasma bag of a sterile set. Unlike conventional methods and devices for the isolation of cryoprecipitate, the invention provides for the sterile isolation of cryoprecipitate in a form which may be stored. It also provides a vessel which may be used directly as an applicator in a surgical setting.

The invention being thus described, various modifications will occur to those skilled in the art and all such variations are intended to be included in the scope of the invention as defined by the following claims.

What is claimed is:

1. A method of isolating cryoprecipitate including the steps of freezing and thawing plasma and subsequently centrifuging the thawed plasma to separate precipitated material therefrom, further comprising the steps of
(A) transferring said plasma to at least one separation vessel having
   (i) a hollow body portion having first and second closed ends and a longitudinal axis
   (ii) a port for said transferring plasma to said vessel, and
   (iii) an elongate nipple extending from and closing the second end, said nipple defining an interior volume in the range of two to five percent of the volume of the hollow body portion, and
(B) orienting a said separation vessel in a fixture during centrifuging such that the nipple end of the vessel assumes a position of greatest g force so as to isolate cryoprecipitate in said nipple,
(C) decanting cryoprecipitate—depleted plasma from said separation vessel via said port,
(D) closing off said port, and
(E) opening said nipple to allow delivery of said cryoprecipitate therefrom without re-mixing or cross contamination.

2. A method according to claim 1 further comprising the step of extruding the cryoprecipitate from the nipple onto a surgical join.

3. A set for the centrifugal separation and handling of cryoglobin, such set comprising:
(A) a first vessel of a size for receiving the plasma fraction of a unit of blood,
(B) at least one separation vessel, each said separation vessel comprising
   (i) a hollow body portion having closed first and second ends and a longitudinal axis
   (ii) means defining a port located at said first end for transferring plasma to or from the separation vessel,
   (iii) an elongate nipple extending from said second end,
   (iv) a tapered portion intermediate said nipple and said hollow body portion for funneling dense material into said nipple during centrifuging, and
(C) flow tube means aseptically interconnecting said first vessel with each said at least one separation vessel for transferring the contents of said first vessel thereto for separation,
each said nipple of a separation vessel having an interior volume in the range of two to five percent of the volume of said hollow body portion, each said port being closable and each said nipple being openable whereby cryoprecipitate-depleted plasma may be decanted from a separation vessel, remaining separated cryoprecipitate may be extruded from the nipple of said separation vessel substantially without cross contamination, and wherein a said nipple has an end with a twist-connect fitting for fluid sealing attachment to a mating device.

4. A set for the centrifugal separation and handling of cryoglobin, such set comprising;
(A) a first vessel of a size for receiving the plasma fraction of a unit of blood,
(B) at least one separation vessel, each said separation vessel comprising
   (i) a hollow body portion having closed first and second ends and a longitudinal axis the body portion is semi-rigid
   (ii) means defining a port located at said first end for transferring plasma to or from the separation vessel,
   (iii) an elongated nipple extending from said second end, the nipple including at an end thereof a conically tapered closed tip portion, the conically tapered closed tip portion defining an area for receiving fluid, which may be sliced off to permit extrusion of plasma from the nipple by squeezing of the body portion,
   (iv) a tapered portion intermediate said nipple and said hollow body portion for funneling dense material into said nipple during centrifuging, and
(C) flow tube means aseptically interconnecting said first vessel with each said at least one separation vessel for transferring the contents of said first vessel thereto for separation,
each said nipple of a separation vessel having an interior volume in the range of two to five percent of the volume of said hollow body portion, each said port being closable and each said nipple being openable whereby cryoprecipitate-depleted plasma may be decanted from a separation vessel, and remaining separated cryoprecipitate may be extruded from the nipple of said separation vessel substantially without cross contamination.

5. A set for the centrifugal separation and handling of cryoglobin, such set formed of substantially rigid material and comprising
(A) a first vessel of a size for receiving the plasma fraction of a unit of blood,
(B) at least one separation vessel, each said separation vessel comprising
   (i) a hollow body portion having closed first and second ends and a longitudinal axis
   (ii) means defining a port located at said first end for transferring plasma to or from the separation vessel,
   (iii) an elongate nipple extending from said second end,
   (iv) a tapered portion intermediate said nipple and said hollow body portion for funneling dense material into said nipple during centrifuging, and
(C) flow tube means aseptically interconnecting said first vessel with each said at least one separation vessel for transferring the contents of said first vessel thereto for separation,
each said nipple of a separation vessel having an interior volume in the range of two to five percent of the volume of said hollow body portion, each said port being closable and each said nipple being openable whereby cryoprecipitate-depleted plasma may be decanted form a separation vessel, remaining separated cryoprecipitate may be extruded from the nipple of said separation vessel substantially without cross contamination, nipple of separation vessel encloses a central cylindrical bore and further comprising
piston means hermetically mounted within the separation vessel in alignment with the bore, and means for releasing the piston and driving it along the bore to extrude from the nipple material contained therein.

6. A set for the centrifugal separation and handling of cryoglobin, such set comprising
(A) a first vessel of a size for receiving the plasma fraction of a unit of blood,
(B) at least one separation vessel, each said separation vessel comprising
   (i) a rigid hollow body portion having closed first and second ends and a longitudinal axis
   (ii) means defining a port located at said first end for transferring plasma to or from the separation vessel,
   (iii) an elongate rigid nipple extending from said second end,
   (iv) a rigid tapered portion intermediate said nipple and said hollow body portion for funneling dense material into said nipple during centrifuging, and
(C) flow tube means aseptically interconnecting said first vessel with each said at least one separation vessel for transferring the contents of said first vessel thereto for separation,
each said port being closable and each said nipple being openable whereby cryoprecipitate-depleted plasma may be decanted from a separation vessel, and remaining separated cryoprecipitate may be extruded from the nipple of said separation vessel substantially without cross contamination.

7. A set according to claim 6, wherein a closed first end of a said separation vessel further includes a hydrophobic micro-porous filter for venting the vessel during transfer of plasma through the port.

8. A set according to claim 6 comprising a plurality of separation vessels in closed sterile fluid communication with a phlebotomy set having a plasma bag.

9. A set according to claim 8, wherein the plurality of separation vessels have a total volume of approximately 250 milliliters.

* * * * *